United States Patent [19]
Jacobs

[11] Patent Number: 6,013,059
[45] Date of Patent: Jan. 11, 2000

[54] MEDICAL APPARATUS

[76] Inventor: Louis Hubert Jacobs, 24 Fernwood Avenue, Newlands, Cape Town, South Africa

[21] Appl. No.: 08/945,103
[22] PCT Filed: Jun. 3, 1996
[86] PCT No.: PCT/US96/08468
 § 371 Date: May 4, 1998
 § 102(e) Date: May 4, 1998
[87] PCT Pub. No.: WO96/38191
 PCT Pub. Date: Dec. 5, 1996

[30] Foreign Application Priority Data

Jun. 2, 1995 [ZA] South Africa .................................. 4565

[51] Int. Cl.$^7$ ............................... A61M 5/32; A61M 5/00
[52] U.S. Cl. .......................... 604/198; 604/110; 604/181; 604/192
[58] Field of Search ..................................... 604/110, 181, 604/194, 192, 198, 187, 263, 197

[56] References Cited

U.S. PATENT DOCUMENTS 4,917,101  4/1990  Horn ........................................ 604/403

*Primary Examiner*—Corrine McDermott
*Assistant Examiner*—Patricia Bianco
*Attorney, Agent, or Firm*—Ladas & Parry

[57] ABSTRACT

Medical apparatus 10 includes a barrel 12 which defines a chamber 14 therein. A sleeve 16 is slidably arranged on the barrel 12 between a first, retracted position and a second, extended position in which a needle of a needle assembly 48 is covered. A coil spring 20 is interposed between the barrel 12 and the sleeve 16 for urging the sleeve 16 to its second position. A locking means 18 locks the spring both in its first position and in its second position.

9 Claims, 1 Drawing Sheet

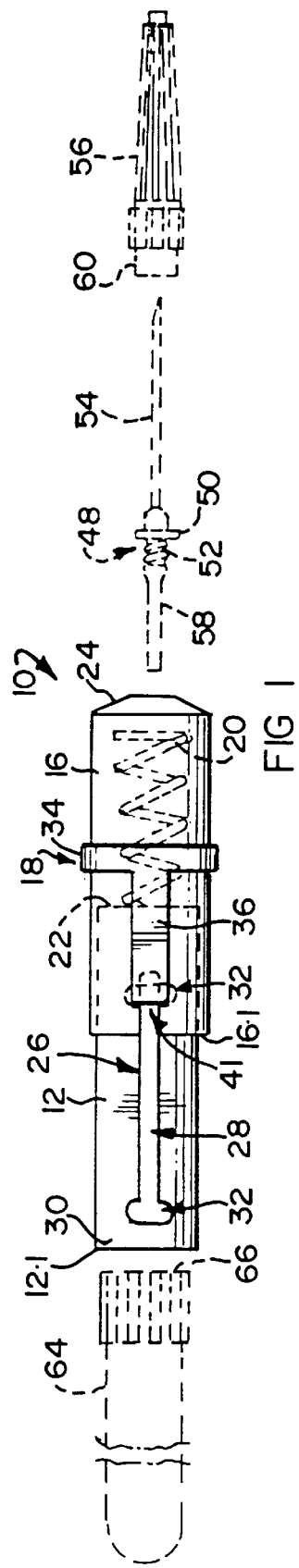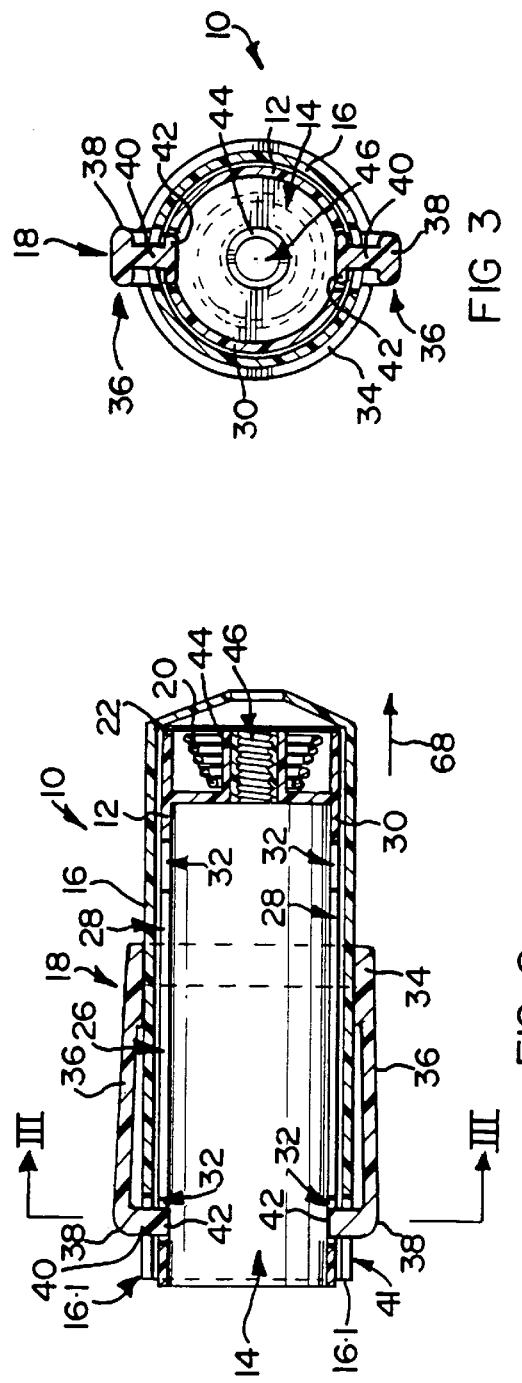

MEDICAL APPARATUS

FIELD OF THE INVENTION

THIS INVENTION relates to medical apparatus. The invention relates particularly to medical apparatus for use in removing fluid from or inserting fluid into a body.

SUMMARY OF INVENTION

According to the invention, there is provided medical apparatus which includes an elongate cylindrical member defining a chamber therein and having a formation at one end for mounting a needle assembly on the cylindrical member;

a protective element slidably mounted relative to the cylindrical member between a first, retracted position in which, in use, a needle of the needle assembly is exposed and a second, operative position in which the needle is covered; and an urging means interposed between the cylindrical member and the protective element for urging the protective element to its second position.

The cylindrical member may be in the form of a barrel partially closed at one end, said partially closed end defining the formation, and the protective element may be in the form of a sleeve slidably or telescopically mounted on the barrel. To ensure reliable operation of the apparatus, the barrel may be circular cylindrical having an outer diameter which is only slightly less than that of an inner diameter of the sleeve, which may also be circular cylindrical, so that the sleeve and barrel can slide relative to each other and jamming is inhibited.

The apparatus may include a locking means for locking the sleeve at least in its first position relative to the barrel. Preferably, the locking means locks the sleeve in both its positions relative to the barrel.

Still further, the apparatus may include a guide means for guiding movement of the sleeve relative to the barrel.

The guide means may include guiding formations defined in the barrel with guide elements, which co-operate with the guiding formations, being carried on the locking means.

The invention has particular application in apparatus used in collecting blood for analysis. Hence, an evacuated vial is removably insertable into the chamber of the barrel for the collection of blood for analysis purposes. Thus, the needle assembly used is a double pointed, blood-collecting needle having a first needle projecting outwardly from the barrel with a second needle projecting into the chamber of the barrel, in use, to pierce a membrane of the vial to cause blood to be charged into the vial. The needles may project in opposite directions from a boss which is mounted on the formation of the barrel. The boss may be screw-threaded and the formation of the barrel may have a correspondingly screw-threaded passage defined therethrough.

The outer needle of the needle assembly is covered by a sheath when not in use. The sheath has a formation which engages the boss of the outer needle. Thus, the free end of the sleeve may have an opening defined therein in which said formation of the sheath is snugly received such that, when the sleeve is retracted from its second position to its first position, the sheath covers the outer needle and its formation is received over the boss. The sheath can then be used to unscrew the boss from the passage of the barrel.

The locking means may comprise a mounting means carried on the sleeve and a locking arrangement extending from the mounting means, the locking arrangement having the guide elements. More particularly, the mounting means may comprise a collar carried on an outer surface of the sleeve and the locking arrangement may comprise a pair of opposed arms extending from the collar in a direction substantially parallel to a longitudinal axis of the sleeve. A free end of each arm may carry one of the guide elements thereon. The guiding formations of the barrel may be in the form of a pair of opposed, longitudinally extending slots defined in a peripheral wall of the barrel. Each slot may be substantially dumbbell-shaped having a laterally enlarged region at each end.

Each guide element may comprise a clip which co-operates with its associated slot in the barrel and which engages said enlarged region of the slot, either when the sleeve is in its first position or in its second position relative to the barrel.

The arms of the locking means may be of a resiliently flexible material. Then, to release the clips from the enlarged regions, pressure is exerted on the arms to urge the clips into the interior of the barrel to effect sliding displacement of the sleeve relative to the barrel. Hence, it will be appreciated that, when the sleeve is in its first position and pressure is applied to the arms to release the clips from the enlarged regions of the slots, the spring bears against the sleeve and the barrel to cause relative displacement of the barrel and the sleeve until the sleeve is in its second position. Then, releasing the arms causes the clips to be received in the other enlarged regions to lock the sleeve in its second position relative to the barrel.

The urging means may comprise a spring. The spring may be a coil spring which is substantially frusto-conical in its relaxed condition, a narrower end of the spring being mounted about the formation of the barrel and a wider end of the spring bearing against a corresponding end of the sleeve.

The invention is now described by way of example with reference to the accompanying diagrammatic drawings.

BRIEF DESCRIPTION OF THE DRAWINGS

In the drawings,

FIG. 1 shows a plan view of medical apparatus, in accordance with the invention, together with components with which the apparatus is used and with a protective element of the apparatus in a second position;

FIG. 2 shows on an enlarged scale, a sectional side view of the medical apparatus with the protective element thereof in its first position; and FIG. 3 shows a sectional end view of the apparatus taken through line III—III in FIG. 2.

DETAILED DESCRIPTION OF THE DRAWINGS

Referring to the drawings, medical apparatus, in accordance with the invention, is illustrated and is designated generally by the reference numeral 10.

The apparatus 10 comprises an elongate cylindrical member or barrel 12 which defines a chamber 14 therein. A protective element in the form of a sleeve 16 is slidably arranged on the barrel between a first position as shown in FIG. 2 of the drawings and a second position as shown in FIG. 1 of the drawings. The apparatus 10 further includes a locking means 18 carried on the sleeve 16 for locking the sleeve 16 both in its first position and in its second position.

An urging means in the form of a coil spring 20 is interposed between an end 22 of the barrel 12 and a free end or nose portion 24 of the sleeve 16. The spring 20 is substantially frusto-conical with its narrower end abutting against the end 22 of the barrel 12 and its wider end abutting against the nose portion 24 of the sleeve 16. Hence, when the sleeve 16 is in its second position relative to the barrel 12 the spring 20 is compressed and, due to its frusto-conical construction, takes up less space than would otherwise be the case.

The apparatus 10 further includes a guide means 26 for guiding sliding movement of the sleeve 16 relative to the barrel 12. The guide means 26 is used in conjunction with the locking means 18.

The guide means 26 comprises a pair of opposed longitudinally extending slots 28 defined in a wall 30 of the barrel 12. As illustrated more clearly in FIG. 1 of the drawings, each slot 28 has an enlarged end region 32 imparting a substantially dumbbell shape to the slot 28.

The locking means 18 includes a collar 34 mounted fast about an outer surface of the sleeve 16. The collar 34 has a pair of opposed arms 36 extending therefrom in a direction parallel to the longitudinal axis of the sleeve 16 towards a distal end 16.1 of the sleeve 16. A free end 38 of each arm 36 has a radially inwardly extending constricted portion 40 (FIG. 3) with a laterally enlarged foot portion 42 being arranged at a free end of the constricted portion 40. The width of the constricted portion 40 of the clip is such that it can pass with clearance through its associated slot 28 and the lateral dimension of the enlarged foot portion 42 of each clip 38 is such that it is a snug fit within each enlarged region 32 of its associated slot 28.

It is to be noted that the sleeve 16, at its distal end 16.1, has a pair of opposed cutaway portions 41 which lie in register with the slots 28 and one of the enlarged regions 32 of the guide means 26 when the sleeve 16 is either in its first position or in its second position.

When the sleeve 16 is either in its first position or in its second position relative to the barrel 12, the arms 36 are splayed outwardly such that the foot portions 42 are received in the relevant enlarged regions 32 of the slots 28 to hold the sleeve 16 in its first position or second position, as the case may be, relative to the barrel 12.

The barrel 12 has, at its end 22, a longitudinally extending formation 44 which defines an internally screw-threaded passage 46. The apparatus 10 is used with a needle assembly 48 (FIG. 1) which has a central boss 50. The boss 50 has an externally screw-threaded portion 52 which is screw-threadedly received in the passage 46 of the formation 44 of the barrel 12. Further, a first, outer needle 54 extends from the boss 50 and, when not in use, is covered by a sheath 56. A second, inner needle 58 projects from the boss 50 in an opposite direction to that of the needle 54.

In use, the sleeve 16 is retained in its second position as shown in FIG. 2. With the sheath 56 attached to the boss 50, the boss 50 of the needle assembly 48 is screwed into the formation 44 of the barrel 12. It is to be noted that the sheath 56 has a formation 60 which is a snug fit in an opening 62 defined in the nose portion 24 of the sleeve 16.

The sheath 54 is removed and the needle 54 is inserted into a person's vein. Once the necessary preparations have been effected, an evacuated vial 64 is inserted into the chamber 14 of the barrel 12 and a membrane at the end 66 of the vial 64 is pierced by the inner needle 58. Due to the evacuated condition of the vial 64 blood from the person is drawn into the vial 64. Once the required quantity of blood has been drawn, the apparatus 10 is removed by withdrawing the needle 54 from the person's vein.

To prevent a user of the apparatus 10 pricking himself with the now-used needle 54 radially inward pressure is exerted on the arms 36 to urge the foot portions 42 of the clips 38 out of engagement with the enlarged end regions 32 of the slots 28 closer to a distal end 12.1 of the barrel 12. When the foot portions 42 of the clips 38 are free of said regions 32 of the slots 28, the sleeve 16 is urged, under the action of the coil spring 20, in the direction of arrow 68 to the position as shown in FIG. 1 of the drawings. The arms 36 are then released such that the foot portions 42 are received within the enlarged end regions 32 of the slots 28 closer to the end 22 of the barrel 12. Hence, the sleeve 16 is then locked in that position relative to the barrel 12.

Whilst the sleeve 16 is in this position, the sheath 56 is mounted on the nose portion 24 of the sleeve 16 by inserting the formation 60 of the sheath 56 into the opening 62 in the nose portion 24 of the sleeve 16. The sleeve 16 is then again retracted to the position shown in FIG. 2 of the drawings whereupon the sheath 60 is received over the boss 50 of the needle assembly 48. The formation 60 of the sheath 56 is a tight fit on the boss 50. For this purpose also, the boss 50 has longitudinally extending vanes (not shown) arranged thereon which engage corresponding ribs in the formation 60 of the sheath 56. The needle assembly 54 is then unscrewed from the barrel 12 for disposal. Those skilled in the art will appreciate that the needle 58 of the needle assembly 48 of the type described is covered by an elastomeric cover so as to inhibit a user pricking himself with the inner needle 58.

Hence, it is a particular advantage of the invention that medical apparatus 10 is provided which will reduce the likelihood of users of the apparatus 10 accidentally pricking themselves with contaminated needles. Thus, the likelihood of the transmission of life-threatening diseases is reduced.

It is claimed:

1. Medical apparatus for use with a blood collecting device, the apparatus including an elongate cylindrical member which defines a chamber in which the blood collecting device is receivable, the cylindrical member having a mounting formation at one end for mounting a needle assembly on the cylindrical member;

a protective element slidably mounted relative to the cylindrical member between a first, retracted position in which, in use, an external needle of the needle assembly is exposed and a second, operative position in which the needle is covered;

an urging means interposed between the cylindrical member and the protective element for urging the protective element to its second position;

a locking means carried by the protective element and which engages locking formations defined in cylindrical member for locking the protective element both in its first position and in its second position relative to the cylindrical member, the locking means being arranged on an external surface of the protective element to be manipulated by a user and the locking means including a locking arrangement which projects through the protective element and the cylindrical member, the locking arrangement having engaging portions which engage the locking formations of the cylindrical member when the protective element is either in its first position or its second position relative to the cylindrical member such that, when pressure is exerted by an user on the locking means, said engaging portions of the locking arrangements are disengaged from said locking formations and are urged into the chamber of the cylindrical member to permit relative movement between the cylindrical member and the protective element; and a guide means for guiding movement of the protective element relative to the cylindrical member, with the guide means including guiding formations defined in the cylindrical member with guide elements, which co-operate with the guiding formations, being carried on the locking means.

2. The apparatus as claimed in claim 1, in which the locking means includes a mounting means carried on the sleeve with the locking arrangement extending from the mounting means.

3. The apparatus as claimed in claim 2, in which the mounting means comprises a collar carried on an outer surface of the sleeve and the locking arrangement includes a pair of arms extending from the collar.

4. The apparatus as claimed in claim 3, in which the guiding formations of the barrel comprise a pair of spaced, longitudinally extending slots defined in a peripheral wall of the barrel, the locking formations being defined at each end of each slot.

5. The apparatus as claimed in claim 4, in which each guide element comprises a clip which co-operates with its associated slot in the barrel, the clip including said engaging portions which engage the locking formations, when the sleeve is either in its first position or its second position relative to the barrel.

6. The apparatus as claimed in claim 5, inclusive in which the urging means comprises a spring.

7. The apparatus as claimed in claim 6, in which the spring is a coil spring which is substantially frusto-conical in its relaxed condition, a narrower end of the spring being mounted about the mounting formation of the barrel and a wider end of the spring bearing against the nose portion of the sleeve.

8. The apparatus as claimed in claim 1, in which the cylindrical member is in the form of a barrel which is partially closed at one end, said partially closed end defining the mounting formation, and in which the protective element is in the form of a sleeve slidably mounted on the barrel.

9. The apparatus as claimed in claim 8, in which the sleeve has a nose portion against which the urging means bears, the nose portion having an opening defined therein in which a covering element is received so that, when the sleeve is in its first position relative to the barrel, the covering element sheathes the external needle to enable the needle assembly to be removed from the mounting formation of the cylindrical member.

* * * * *